United States Patent [19]

Quesenberry

[11] Patent Number: 6,068,836
[45] Date of Patent: *May 30, 2000

[54] CELL COMPOSITIONS FOR USE IN TRANSPLANTATION

[75] Inventor: Peter J. Quesenberry, Shrewsbury, Mass.

[73] Assignee: University of Massachusetts, Boston, Mass.

[ * ] Notice: This patent is subject to a terminal disclaimer.

[21] Appl. No.: 08/849,276

[22] PCT Filed: Nov. 22, 1995

[86] PCT No.: PCT/US95/15205

§ 371 Date: Aug. 25, 1997

§ 102(e) Date: Aug. 25, 1997

[87] PCT Pub. No.: WO96/15813

PCT Pub. Date: May 30, 1996

Related U.S. Application Data

[63] Continuation-in-part of application No. 08/344,080, Nov. 23, 1994, Pat. No. 5,665,350.

[51] Int. Cl.$^7$ .......................... A01N 63/00; A01N 43/04; C12N 5/00; C12N 5/08

[52] U.S. Cl. ................... 424/93.21; 424/93.1; 424/93.2; 424/93.7; 435/325; 435/372; 435/383; 435/455

[58] Field of Search ................................. 424/93.1, 93.2, 424/93.21, 93.7; 435/325, 372, 383, 455; 514/44

[56] References Cited

U.S. PATENT DOCUMENTS

| | | | |
|---|---|---|---|
| 4,396,601 | 8/1983 | Salser et al. | 424/94.5 |
| 5,032,407 | 7/1991 | Wagner et al. | 800/23 |
| 5,061,620 | 10/1991 | Tsukamoto et al. | 435/7.21 |
| 5,437,994 | 8/1995 | Emerson et al. | 435/373 |
| 5,665,350 | 9/1997 | Quesenberry | 424/93.21 |

FOREIGN PATENT DOCUMENTS

| | | |
|---|---|---|
| 2086844 | 7/1994 | Canada . |
| 94/11493 | 5/1994 | WIPO . |
| PCt/US95/ 15205 | 11/1995 | WIPO . |

OTHER PUBLICATIONS

Barlogie, B. "Hemopoietic stem cell transplant for multiple myeloma (MM)", *Leukemia*, 7:1095, (1993).
Biron, P. et al., "Autologous Bone Marrow Transplantation: Proceedings of the First International Symposium".
Breacher, G. et al. "Special proliferative sites are not needed for seeding and proliferation of . . . syngeneic mice", *PNAS USA* 79:5085–5087, (1982).
Cheson, B.D. et al., "Autologous bone . . . future directions", *Ann. Intern. Med.* 110(1):51–56, (1989).
Crittenden R. et al., "Repetitive Marrow . . . Gene Therapy", *Experimental Hematology*, 21:1016, Abstract 30.
Culver K. et al., "Gene therapy for cancer", *TIG*, 10:174–178, (1994).

Harrison, D., "Competitive Repopulation in Unirradated Normal Recipients", *Blood*, 81:2473–2474, (1993).
Hodgson, C., "Advanced in vector systems for gene therapy", *Exp. Opin. Ther. Patents*, 5(5):459–468, (1995).
Kohn, D., "The current status of gene therapy using hematopoietic stem cells", *Current Opinion in Pediatrics* 7:56–63, (1995).
Marshall, E., "Gene Therapy's Growing Pains", *Science*, 269:1050–1055 (1995).
Miller, N. et al., "Targeted vectors for gene therapy", *The FASEB Journal*, 9:190–198, (1995).
Peters, S.Q. et al., "Cytokine Incubation of Murine Marrow Cells Impairs Repopulating Capacity in normal Non–myeloablated) Hosts", *Experimental Hematology*, 22(8):823, abstract 547 (1994).
Peters, W.P., "The Rationale for High–Dose . . . in Treating Breast Cancer", *AMBT supra*, 189–195, (1985).
Ramshaw, H.S. et al., "Effect of cell cycle on the engraftment . . . unmyeloablated hosts", *Experimental Hematology*, 22:823, abstract 548.
Saxe, D.F. et al., "Transplantation of Chromosomally . . . Hematopietic Stem Cell Depletion", *Exp. Hematol.*, 12:277–283, (1984).
Stewart et al., "Long–Term Engraftment of . . . Nonmyeloablated Mice", *Blood*, 81(10):2566–2571, (1993).
Sullivan, K.M., "Marrow transplantation . . . hematopoises", *Leukemia*, 7:1098–1099 (1993).
Takvorian, T. et al., "Prolonged disease–free survival . . . with a poor prognosis", *N. Engl. J. Med.*, 316:1499–1505, (1987).
Wheeler C., et al., "Cyclophosphamide, carmustine, . . . and non–Hodgkin's Lymphoma:a dose–finding study", *J. clin. Oncol.*, 8(4):548–656, (1990).
Yeager, A.M. et al., "Autologous bone marrow . . . with 4–hydroperoxycyclophosphamide", *N. Eng. J. Med.*, 315(3):141–147, (1986).
Orkin and Motulsky, Report and recommendations of the panel to assess the NIH investment in research on gene therapy, Dec. 1995.
Friedmann, T. Overcoming the obstacles to gene therapy. Sci. Am. pp. 96–101, Jun. 1997.
Verma et al. Gene therpy—promises, problems, and prospects. Nature 389:239–242, Sep. 1997.
Marshall, E. Gene therapy's growing pains. Science 269. 1050–1055, Aug. 1995.
Sandstrom et al. Review: Serum–free media for cultures of primitive and mature hematopoietic cells. Biotechnology and Bioengineering 43: 706–733, Apr. 1994.
Stewart et al. Long–term engraftment of normal and post–5–fluorouracil murine marrow into normal nonmyeloablated mice. Blood 81(10) 2566–2571, May 1993.
Brecher et al. Special proliferative sites are not needed for seeding and proliferation of transfused bone marrow cell in normal syngeneic mice. Proc. Natl. Acad. Sci. USA 79: 5085–5087, Aug. 1982.

*Primary Examiner*—Deborah Crouch
*Assistant Examiner*—Anne-Marie Baker
*Attorney, Agent, or Firm*—Fish & Richardson P.C.

[57] ABSTRACT

Methods for the preparation of bone marrow stem cell compositions for use in transplantation therapy and ex vivo gene therapy of a mammal. The methods involve the use of quiescent stem cells for transplantation therapy and quiescent transfected stem cells for ex vivo gene therapy.

20 Claims, 5 Drawing Sheets

CELL COMPOSITIONS FOR USE IN TRANSPLANTATION

CROSS-REFERENCE TO RELATED APPLICATIONS

This application is a continuation-in-part of earlier filed U.S. application Ser. No. 08/344,080, filed Nov. 23, 1994, which application is incorporated herein by reference in its entirety and is the basis of a claim for priority under 35 U.S.C. § 120.

STATEMENT AS TO FEDERALLY SPONSORED RESEARCH

This invention was made at least in part with funds from the Federal government, and the government therefore has rights in the invention.

BACKGROUND OF THE INVENTION

The invention relates to the field of stem cell engraftment and human ex vivo gene therapy.

Bone marrow transplantation is often accompanied by marrow cytotoxic therapy to create marrow space or niches. The usual method of creating such niches is by irradiation and/or chemotherapy treatment. This practice has been challenged by Brecher, Saxe and colleagues, who demonstrated that bone marrow cells (e.g., hematopoietic stem cells) engraft into normal non-myeloablated hosts (Brecher, G. et al. (1982) PNAS USA 79:5085; and Saxe, D. F. et al. (1984) Exp. Hematol. 12:277). These investigators showed varying levels of engraftment up to 25% after infusion of normal bone marrow into non-myeloablated hosts.

One theoretical approach to transplantation involves procurement of stem cells for transplantation followed by expansion of the stem cells to increase their number prior to infusion into the host. Cellular expansion and/or induction into active cell cycling is accomplished by contacting cytokines or other agents, such as 5-fluorouracil, with the stem cells in vivo, if expansion occurs prior to collection of stem cells; or in vitro, if expansion occurs following collection of stem cells. Long-term repopulation of bone marrow with cytokine-treated cells has been assessed in vivo (Bodine D. M., Blood, 79:913, 1992; Szilvassy S. J. and Cory, S., Blood 84:74, 1994; Li, C. L. and Johnson, G. R. Blood 84:408, 1994; and Ramshaw, H. S. et al., Experimental Hematology, 22:823, No. 548, 1994).

Additionally, cytokines have been used in various combinations to enhance retroviral integration into stem cells by increasing the percent of stem cells in the process of active cell cycle. In vitro cytokine incubations have been used to induce active cell cycling in hematopoietic cells to facilitate retroviral integration in various gene therapy approaches (Bodine D. M. et al., Exp Hematol 19:206, 1991; Szilvassy S. J. and Cory, S., Blood 84:74, 1994; and Kittler, E. L. W. et al., Blood 84:344, 1994 (abstr. suppl I)). Subsequent to retroviral integration, these actively cycling transfected stem cells are introduced into a mammal so that they engraft in the bone marrow of the mammal. Thus the success of ex vivo gene therapy is dependent not only on the efficiency of retroviral integration, but also on the efficiency of transfected stem cell engraftment.

There is a great need for methodologies to enhance engraftment of stem cells in a host mammal for the purpose of improved human bone marrow transplantation therapy as well as for improved human ex vivo gene therapy.

SUMMARY OF THE INVENTION

Applicant discloses that rendering cells quiescent prior to transplantation results in improved long term engraftment, i.e., for time periods greater than approximately 6 weeks post-transplantation. Accordingly, the invention features stem cell compositions and methods of preparing stem cell compositions for transplantation or ex vivo gene therapy that significantly enhance engraftment of the transplanted stem cells, wherein the stem cells are expanded to produce a population of expanded stem cells. The expanded stem cells are next treated so that a majority of them become quiescent stem cells to form the stem cell composition that is introduced into a mammal by standard stem cell transplantation techniques. In preferred embodiments the mammal is a non-myeloablated or a myeloablated host mammal, preferably a human patient.

Stem cells are expanded and/or treated to enter active cell cycling in vivo or in vitro by methods well known to those skilled in the art and include, but are not limited to, the administration of a cytokine, e.g., stem cell factor (Steel factor), IL-3-CHO, IL-6, IL-11, and the like, to the stem cell in vivo or in vitro; and administration of 5-fluorouracil (5-FU) in vivo.

Expanded and/or actively cycling stem cells are treated to become quiescent according to the invention by methods well known to those of ordinary skill in the relevant arts and include, but are not limited to, serum starvation and removal of the expanding or cell cycling-inducing agent. Cells are judged to be quiescent when fewer than 30%, preferably fewer than 10%, more preferably fewer than 5% of the cells are judged to be progressing through the cell cycle as determined by the high specificity tritiated thymidine [$^3$HtdR] suicide technique which selects only fully proliferating cells, i.e., replicating cells. Quiescent cells can also be observed by the lack of incorporation of a radio-labelled nucleotide into the DNA of a representative portion of the cell population of interest. Quiescent cells are also observed as exhibiting a single DNA peak as measured by flow-cytometry (a single peak indicates that the cells are quiescent, while more than one peak indicates DNA synthesis).

The invention also features stem cell compositions and methods of preparing stem cell compositions for use in ex vivo gene therapy in which the stem cells are induced to proliferate to enhance retroviral vector integration, and then induced to become quiescent prior to introduction into a mammal. The invention also features the gene therapy method. In preferred embodiments, the therapeutic method is used for treating an inherited, an acquired, or a metabolic deficiency in a mammal (such as a human). For example, the transfected stem cells may contain expressible DNA for the production of antisense RNA to reduce the expression of an endogenous gene of the mammal. In other preferred embodiments, the transfected stem cell may contain DNA encoding a protein capable of preventing or treating an inherited or acquired disease, e.g., Factor VIII deficiency in hemophilia, cystic fibrosis, and adenosine deaminase deficiency.

Infused cells or their progeny preferably contain a marker such that the infused cells can be observed in a population of host cells for the purpose of measuring the level of engraftment.

Another embodiment of the invention is a method of transplanting a predetermined number of quiescent stem cells into a non-myeloablated host mammal in which a first fraction of the stem cells is introduced into the host mammal at a first point in time followed by introducing thereafter the remaining cells in at least 5, and not greater than 15, additional administrations. Preferably each administration is spaced from the other by at least 12 hours. At a final point in time a final fraction of the predetermined number of cells is introduced such that all of the cells have been introduced into the host mammal.

The invention also features a method of ex vivo gene therapy in which transfected pluripotent hematopoietic stem cells are treated to become quiescent transfected stem cells. A predetermined number of the transfected stem cells are introduced into the host mammal such that a first fraction of the cells are introduced at a first point in time followed by introducing thereafter the remaining cells in at least 5, and not greater than 15, additional administrations, each administration being spaced from the other by at least 12 hours. At a final point in time, a final fraction of the predetermined number of transfected quiescent stem cells is introduced such that all of the original predetermined number of cells have been introduced into the host mammal.

In a preferred embodiment of the scheduled transplantation for enhancement of engraftment of quiescent stem cells or quiescent transfected stem cells, the scheduled transplantation involves a predetermined number of cells wherein the number is at least $1 \times 10^8$ cell/kg body weight of the host mammal and not more than $8 \times 10^9$ cell/kg body weight of the host mammal.

In another preferred embodiment of the scheduled transplantation methods, the fractions of the predetermined stem cells are substantially equal in number of cells. Preferably, the introduction of the quiescent stem cells, or quiescent transfected stem cells, occurs at least 5, and not more than 15, days after the first introduction of a fraction of the stem cells. Preferably, the introductions of said cells are spaced approximately equally in time from the first introduction to the final introduction of the cells.

In another embodiment of the invention, a method of providing short term and long term bone marrow transplantation is provided. A population of expanded stem cells is divided into first and second fractions. The first fraction is used to prepare a first cell compositions, and is introduced into a host mammal by a single administration, or preferably by multiple, scheduled administrations. The second fraction is induced to become quiescent prior to introduction into the host mammal, and is used as the second cell composition, as a single administration or preferably by the scheduled administration of multiple fractions.

In another embodiment of the invention, a method of providing short term and long term ex vivo gene therapy is provided. A population of expanded transfected stem cells is divided into first and second fractions. The first fraction is introduced into a host mammal by a single administration of cells or preferably by the scheduled administration of multiple fractions. The second fraction of expanded transfected stem cells is induced to become quiescent prior to introduction into the host mammal as a single administration or preferably by the scheduled administration of multiple fractions.

In yet another embodiment of the invention, a method of providing short term and long term bone marrow transplantation is provided in which a population of expanded stem cells is separated into fractions, a first fraction being enriched in short term repopulating stem cells, and a second fraction being enriched in long term repopulating stem cells. The first fraction of expanded, actively cycling stem cells is introduced into a host mammal for short term engraftment (engraftment up to approximately 6 weeks post-transplantation). The second fraction of expanded, actively cycling stem cells is induced to become quiescent prior to introduction into a host mammal, thus allowing long term engraftment (engraftment after approximately 6 weeks post-transplantation).

In another embodiment of the invention, an ex vivo gene therapy method is provided in which a population of expanded stem cells is separated into fractions, a first fraction being enriched in short term repopulating stem cells, and a second fraction being enriched in long term repopulating stem cells. According to the method, transfection of the expanded stem cells, e.g., by retroviral transfection, with exogenous DNA is performed prior to separation of the stem cells into fractions enriched with early or late repopulating stem cells. According to the method, transfection is optionally performed after separation of the stem cells into fractions. The first fraction of transfected expanded, actively cycling stem cells is introduced into a host mammal for short term engraftment and short term ex vivo gene therapy. The second fraction of transfected expanded, actively cycling stem cells is induced to become quiescent prior to introduction into a host mammal, thus allowing long term engraftment and long term ex vivo gene therapy.

By the term "stem cell" or "hematopoietic stem cell" is meant a pluripotent cell of the hematopoietic system capable of differentiating into cells of the lymphoid and myeloid lineages.

By the term "transfected stem cell" is meant a stem cell into which exogenous DNA or an exogenous DNA gene has been introduced by retroviral infection or other means well known to those of ordinary skill in the art.

By the term "ex vivo gene therapy" is meant the in vitro transfection or retroviral infection of stem cells to form transfected stem cells prior to introducing the transfected stem cells into a mammal.

By the term "quiescent stem cell" is meant a stem cell in the $G_1$ or $G_0$ phase of the cell cycle. A population of cells is considered herein to be a population of quiescent cells when at least 50%, preferably at least 70%, more preferably at least 80% of the cells are in the $G_1$ or $G_0$ phase of the cell cycle. Quiescent cells exhibit a single DNA peak by flow-cytometry analysis, a standard technique well known to those of ordinary skill in the arts of immunology and cell biology. Another technique useful for determining whether a population of cells is quiescent is the addition of a chemical agent to the cell culture medium that is toxic only to actively cycling cells, i.e., DNA synthesizing cells, and does not kill quiescent cells. Non-exclusive examples of such chemical agents include hydroxyurea and high specific activity tritiated thymidine ($^3$HtdR). A population of cells is evaluated as to the percent in an actively cycling state by the percent of the cell population killed by the chemical agent. A cell population in which in vitro tritiated thymidine killing is less than approximately 30%, preferably less than approximately 10%, more preferably less than approximately 5%, is considered to be quiescent.

By the term "early repopulating stem cells" is meant stem cells which are capable of engrafting into the bone marrow of a host mammal within approximately 6 weeks post-transplantation.

By the term "late repopulating stem cells," also termed "long-term repopulating cells" is meant myelolymphoid stem cells which are capable of engrafting into the bone marrow of a host mammal after approximately 6 weeks post-transplantation.

By the term "engrafting" or engraftment" is meant the persistence of proliferating stem cells in a particular location over time. Thus, early repopulating stem cells do not persist for more than about 6 weeks, whereas late repopulating stem cells persist for longer, and preferably much longer, than about 6 weeks.

Cycling stem cells can be treated to become quiescent by serum or isoleucine starvation. Quiescence can also be induced by reduction of nutrients in the culture medium such that the cycling stem cells enter and remain in the $G_1$ or $G_0$ phase of the cell cycle while the nutrient level is reduced. These methods can be used alone or in combination.

By the term "expanded population" is meant a population of cells, wherein at least 50% of the cells have divided at least once. In certain embodiments of the invention, the cells may be induced to divide by the administration of cell cycling agents such as 5-FU and/or cytokines such as IL-3-CHO, IL-6, IL-11, and other growth stimulating factors well known to those of ordinary skill in the art of immunology.

By the term "non-myeloablated host mammal" is meant a mammal which has not undergone irradiation, or other treatment (such as chemical treatment) well known to those of ordinary skill in the art, to cause the death of the bone marrow cells of the mammal.

By the term "myeloablated host mammal" is meant a mammal which has undergone irradiation, or other treatment, such as chemical treatment, well known to those of ordinary skill in the art, to cause the death of at least 50% of the bone marrow cells of the mammal.

The invention provides methods for the treatment of myelolymphoid cell disorders and stem cell compositions for use in the treatments. The invention affords unique and critical advantages over previous methods. Specifically, the invention provides for increased engraftment of transplanted cells by transplantation of quiescent stem cells or quiescent transfected stem cells into a myeloablated or a non-myeloablated host mammal. Enhanced stem cell engraftment is useful for treating diseases caused by impaired function of bone marrow cells. Examples of such diseases include, but are not limited to, lymphoma, multiple myeloma, breast cancer, testicular cancer, leukemias, congenial hemolytic anemias (sickle cell anemia and thalassanemia) and some immunodeficiency diseases, e.g., acute leukemia, Hodgkin's and non-Hodgkin's lymphoma, and neuroblastoma. Ex vivo gene therapy is also enhanced by the improved engraftment of transfected stem cells according to the method of the invention. Such transplantation of quiescent stem cells and the resultant increased engraftment permits amplification of a desired therapeutic effect.

The improved engraftment achieved using the methods of the invention is also useful in high-dose chemotherapy regimens. The hematologic toxicity observed with multiple cycles of high-dose chemotherapy is relieved by conjunctive administration of autologous hematopoietic stem-cells. Diseases for which reinfusion of stem cells (cells not induced to be quiescent) has been described include acute leukemia, Hodgkin's and non-Hodgkin's lymphoma, neuroblastoma, testicular cancer, breast cancer, multiple myeloma, thalassemia, and sickle cell anemia (Cheson B. D., et al. (1989) Ann Intern Med. 30 110:51–65; Wheeler, C. et al. (1990) J. Clin. Oncol. 8:648–656; Takvorian, T. et al. (1987) N. Engl. J. Med. 316:1499–1505; Yeager, A. M. et al. (1986) N. Eng. J. Med. 315:141–147; Biron, P. et al. (1985) in *Autologous Bone Marrow Transplantation: Proceedings of the First International Symposium*, Dicke, K. A. et al., eds, p. 203; Peters, W. P. (1985) ABMT, supra, p. 189; Barlogie, B. (1993) Leukemia 7:1095; Sullivan, K. M. (1993) Leukemia 7:1098–1099). Treatment of such diseases can be improved by the method of the present invention of administering cells known to be quiescent and therefore capable of engrafting at an increased level in a host mammal which has or has not been subjected to myeloablation.

Another advantage of the invention is the reduced risk to the recipient of the transplanted cells since no myeloablation is necessary to achieve superior short and long-term engraftment in the non-myeloablated host mammal.

Another advantage of the invention is that under conditions in which the host is myeloablated, the method of the invention provides superior long term engraftment by administering cells known to be quiescent.

Another advantage of the invention is the ability to use bone marrow, mobilized peripheral blood, and cord blood stem cells in clinical transplant therapy or ex vivo gene therapy.

An advantage of the present invention is its ability to provide useful methods for increased engraftment of stem cells or transfected stem cells by controlling the cell cycle state of the transplanted cells.

Other features and advantages of the invention will be apparent from the following detailed description thereof, and from the claims.

DETAILED DESCRIPTION

Methods for the enhancement of bone marrow stem cell engraftment are provided for use in transplantation therapy and ex vivo gene therapy of a mammal. The methods involve the induction of cellular expansion of the stem cells and the induction of the cells to become quiescent prior to transplantation of the stem cells for transplantation therapy and for ex vivo gene therapy.

Short-term in vitro incubation of murine or human marrow cells with a variety of single cytokines or growth factor combinations results in expansion of hematopoietic progenitor cells (HPC) as assayed in in vitro colony systems including multipotent colony-forming cells, long term culture-initiating cells (LTC-IC), and low- and high-proliferative potential colony-forming cells (LPP- and HPP-CFCs).

In one study detailed below, in vitro cytokine-treated cells, as opposed to cells harvested after in vivo chemotherapy, were administered in competition with untreated cells and analyzed for their contribution to engraftment. Primitive hematopoietic cells induced to divide and proliferate by cytokines in culture are inhibited in the ability to engraft (possess an engraftment defect) prior to approximately 6 weeks post-transplantation. The defect is related to cell cycle activation of the donor cells. Competitive transplant studies in nonlymphomyeloablated hosts demonstrated marrow cells harvested 6 days after in vivo treatment of mice with 5-FU exhibit an engraftment defect and that the defect is no longer present if the cells are harvested 35 days after treatment with 5-FU. Using the same animal model, a cytokine-induced engraftment defect was shown. In both cases, the engraftment defect correlated with cell-cycle activation.

Protocols designed to promote mitosis of hematopoietic progenitors for retroviral gene transfer frequently contain cytokine combinations including SCF, IL-3, IL-6, and IL-11 rendering them unlikely to engraft. Enhancing engraftment efficacy of cytokine-treated stem cells by reversing cell-cycle-related defects are useful both to improve the clinical potential for cytokine-expanded stem cells and for gene therapy approaches.

In Examples 7 and 8, a report is provided of two competitive studies in which cytokine-treated cells, which were not pretreated in vivo to proliferate (e.g., day 2 post 5-FU), competed with noncultured fresh marrow cells in lethally irradiated recipients for engraftment. The effects on engraftment of in vitro culture of marrow cells with interleukin-3 (IL-3), IL-6, IL-11, and stem cell factor (SCF) on progenitor cell expansion, cell-cycle status, and competitive repopulation in vivo was examined.

Two competitive murine transplant models using irradiated host mice were employed to examine the engraftment potential of marrow cells cultured for 48 hours with the cytokines mSCF, IL-3, IL-6, and IL-11. The first model, which uses the Ly-5.l/Ly-5.2 congenic B6.SJL and C57BL/6 strains, allows distinction of donor- and host-derived cells with monoclonal antibodies specific for the alleles of Ly-5; the second model uses BALB/c mice, allowing for the detection of male donor cell DNA sequences in female recipients.

General Procedures

Animals

Male and female BALB/c mice were obtained from the Jackson Laboratory (Bar Harbor, ME). C57BL/6 (Ly5.2) and B6.SJL-Ly5a (Ly5.1) mice were purchased from The Jackson Laboratories (Bar Harbor, Me.), and BALB/c mice were purchased from Charles River Laboratories (Wilmington, Mass.). All animals were maintained in virus-free conditions and were given food and acidified water ad libitum. Mice were purchased at either 16 to 18 g or 18 to 22 g and were housed for minimum of 1 week before experimental use.

Tritiated Thymidine Suicide Assay

A standard in vitro $^3$HTdR suicide technique (Iscove, N. N. et al. (1970) Proc. Soc. Exp. Med. 134:33; and Quesenberry, P. J. and Stanley, K. (1980) Blood 56:1000), well known in the art, was performed as follows. A population of $5\times10^6$ marrow cells per ml were incubated at 37° C. for 20 minutes in Hanks' balanced salt solution (HBSS) containing 200 $\mu$Ci per ml $^3$H-TdR (New England Nuclear: specific activity=20.0 Ci/mmol/L) or a concentration of nonradioactively labelled thymidine equivalent to that in the $^3$HTdR incubation. After incubation, the cell suspensions were washed three times and then plated at an equivalent cell density of 25,000 per dish based on the original counts for progenitor cell growth in vitro in soft agar as described above. The fraction of cells actively cycling was determined by percent reduction of HPP-CFC induced by $^3$HTdR exposure.

Soft-agar Colony-forming Assay

To evaluate the colony forming ability of test cells, in vitro agar colony-forming assays were performed as follows. Both freshly procured uncultured cells and cells obtained after 48 hours in culture were counted and placed at a cell density of 25,000 per 35-mm plastic petri dish in a double-layer nutrient agar system. Underlays were A-MEM with 15% FCS supplemented with vitamins, glutamine, and growth factors (colony-stimulating factor [CSF-1], granulocyte-macrophage-CSF [GM-CSF], G-CSF, IL-1α, IL-3, mSCF, and bFGF). Target cells were included in a 0.5-ml overlay with a final agar concentration of 0.33%. Dishes were gassed with a mixture of 5% $O_2$, 10% $CO_2$, and 85% $N_3$, and incubated at 37° C. for 14 days. Four dishes were prepared from each animal. Dishes were scored on a dissecting microscope for LPP-CFC (all cell clusters with more than 50 cells and not fulfilling HPP-CFC criteria) and HPP-CFC (highly dense colonies greater than 0.5 mm in diameter or moderately dense colonies greater than 1.0 mm in diameter) (Peters, S. O. et al., (1995) Exp. Hematol. 23:461).

Stem Cell Sorting

A non-limiting method of sorting a population of stem cells into populations enriched in either early or late repopulating stem cells is provided below. The method utilizes differential staining characteristics of stem cells to allow fluorescence-activated cell sorting (FACS). It is understood the appropriate antibodies are chosen by one of ordinary skill in the art to be appropriate for the cell strain being manipulated.

In an exemplary method for isolating late repopulating stem cells (identified as Hoechst low, rhodamine low, cells by FACS analysis), cells are prepared for FACS by obtaining the cells from the femurs and tibiae of mice (e.g., C57BL/6 mice, or the like) by flushing using a 2.5 ml syringe with a 21-gauge needle. After washing, the bone marrow cells are resuspended in PBS/2%BSA (phosphate buffered saline/2% bovine serum albumin) and passed through a 40 $\mu$m filter (Falcon #2340, VWR #21008–949, for example). Filtered cells are diluted to $10^7$ cells/ml with PBS and centrifuged for 20 minutes, 1000× g (1800 rmp) 4° C. Cells are collected and washed with PBS/2%BSA and centrifuged at 1500 rmp, 10 minutes at 4° C. Collected cells are resuspended to $10^8$ cells/ml in PBS/2%BSA and incubated for 15 minutes at 4° C. with an equal volume of antibody mixture: Ter 119, 0.1 $\mu$g/ml; B220 (15 $\mu$l/$10^8$ cells, Nature, 289:681 (1981); MAC-1 (15 $\mu$l/$10^8$ cells); GR-1 15 $\mu$l/$10^8$ cells; 7/4 (400 $\mu$l/$1.5\times10^8$ cells, Immunogenetics, 18:229 (1983)); Lyt-2 (½0 final dilution, BD/Collaborative—lot 903514); L3T4 (½0 final dilution, BD/Collaborative—lot 903554); YW25.12.7 (1/10 final concentration, Mol. Cell Probes, 1:297 (1987)).

Following incubation with the antibodies, the cells are diluted to 50 ml with PBS/2%BSA and centrifuged at 1500 rpm for 10 minutes. Cells are collected and the cell suspension volume is adjusted to 2 ml with PBS/2%BSA. To the cells is added a 2 ml suspension of washed DYNAL-BEADS450® (Dynal Inc., Oslo, Norway) dropwise with swirling. The cell/bead mixture is centrifuged for 3 minutes at 40 rpm and the cells are resuspended by pipetting. Suspension volume is adjusted to 7 ml and the beads together with the cells bound to them are removed magnetically. The mixture is washed with 40 ml PBS/2%BSA and centrifuged for 10 minutes at 1500 rpm at 4° C.

Cells are collected and resuspended to $10^6$ cells/ml, rhodamine is added to 0.1 $\mu$g/ml final concentration and incubated 20 minutes at 37° C. in the dark. The cells are centrifuged 10 minutes at 1500 rpm, and the cells are resuspended to $10^6$ cells/ml with 10 $\mu$M Hoechst and incubated for 1 hour at 37° C. Cells are washed in cold PBS/2%BSA, centrifuged, collected, and resuspended to approximately $1-5\times10^6$ cells/ml. Cells are evaluated on a FACS instrument using Blast window, 3% Hoechst, and 10% rhodamine.

In an exemplary procedure for collecting separate populations of cells enriched in early or late repopulating stem cells the following conditions can be used (Li, C. L. and Johnson, G. R. Blood 84:408 (1994)), with the antibodies chosen for the specific cell mixture being analyzed. Cells are prepared for FACS by obtaining the cells from the femurs and tibiae of mice as described above. After washing, the bone marrow cells are resuspended in 10 ml balanced salt solution containing 5% fetal calf serum (BSS.FCS) and 0.1 μg/ml rhodamine 123 (Eastman Kodak Co., Rochester, N.Y.), and incubated at 37° C. for 30 minutes.

After washing once, the cells are resuspended in 10 ml fresh BSS.FCS and incubated at 37° C. for 30 minutes. The cell suspension is then diluted further by the addition of 10 ml BSS.FCS, layered on top of FICOLL® (Pharmacia Inc. Piscataway, N.J.), and centrifuged at 1,600× g for 10 minutes at room temperature. Light-density, viable bone marrow cells are recovered and washed with 10 ml of BSS.FCS. After washing and resuspension in 3 ml of BSS.FCS, the cells are incubated on ice for 15 minutes with a mixture of rat monoclonal antibodies (MoAbs), GK1.5, 53-6.72, 53-7.3.13, RA3-6B2, M1/70.15.11.5, and RB6-8C5, reactive with specific antigens on mature T, B, and myeloid cells (neutrophils and monocytes/macrophages). After washing with 10 ml BSS.FCS and centrifugation through an FCS underlayer, the cells are resuspended in 1 ml of BSS.FCS, mixed together with 1 ml of prewashed magnetic DYNAL-BEADS® (Dynalbeads M450; Dynal Inc. Oslo, Norway), and incubated for 20 minutes at 4° C. with constant mixing.

After diluting the mixture by adding 5 ml of fresh BSS.FCS, the beads together with the cells bound to them, are removed magnetically. This procedure is repeated twice to both bead and bead-free cell populations. The bead-free cell fractions (lineage antigen depleted, Lin-) are pooled, centrifuged, and then stained sequentially at 4° C. for 15 minutes each in 0.5 ml of phycoerythrin (PE)conjugated goat antirat Ig (mouse absorbed), biotinylated E13-161.7 MoAb (anti-Ly6A/E), and Texas red-avidin. Each staining step is followed by a washing step with 10 ml of BSS.FCS.

The bone marrow cells are preincubated with 50 μg normal rat Ig for 2 to 3 minutes before the addition of biotinylated E13-161.7 MoAb. After the final wash, the cells are resuspended in 3 ml of BSS.FCS containing 10 μg/ml propidium iodide (Calbiochem Corp, La Jolla, Calif.), and filtered through a 63-μm pore size nylon screen. FACS is performed using an unmodified FACStar-Plus instrument (Becton Dickinson Immunocytometry Systems, San Jose, Calif.). Cells are positively sorted into Rh123$^{lo}$, Lin-, Ly6A/E+ (long term repopulating cells of this strain), and Rh$^{med/hi}$, Lin-, Ly6a/E+ (short term repopulating cells of this strain) populations. All cells are kept at 4° C. throughout the whole procedure. After completion of cell sorting, the deflected cells are centrifuged at 1,500 rpm for 5 minutes, resuspended, and counted using a hemocytometer.

Induction of Cellular Quiescence

Non-limiting examples or procedures for inducing stem cells to become quiescent (enter the $G_0$ or $G_1$ phase of the cell cycle) are provided herein. According to the methods of the invention, stem cells are initially induced to enter the cell cycle and expand for the purpose of increasing cell numbers or to provide cellular conditions conducive to retroviral integration. Cellular expansion is induced by the addition of one or more cytokines to the growth medium as described herein.

Prior to transplantation, the expanded stem cells are induced to become quiescent by decreasing the concentration of cytokines, nutrient starvation, addition of inhibitors of cell cycling, or growth on adherent cell cultures. These procedures are described below.

To induce quiescence, cells grown in medium containing a cytokine (such as 50 ng/ml Steel factor alone) or cytokines (a mixture of IL-3 (50 U/ml), IL-6 (50 U/ml), IL-11 (50 ng/ml), and Steel factor (50 U/ml)), are transferred to medium containing 0.5 ng/ml Steel factor as the only cytokine. Cells are monitored for quiescence at days 1, 2, 3, 5, and 7 post-transfer by procedures described herein for determining entrance into $G_0$ or $G_1$ phase of the cell cycle.

Another procedure for inducing quiescence is to transfer cells growing in medium containing a cytokine (such as 50 ng/ml Steel factor alone) or cytokines (a mixture of IL-3 (50 U/ml), Il-6 (50 U/ml), Il-11 (50 ng/ml), and Steel factor (50 U/ml)) to a medium containing the same cytokines but deprived of the nutrient isoleucine. Such nutrient deprivation causes the cells to enter the $G_0$ or $G_1$ phase of the cell cycle. Cells are monitored at 1, 2, 5, and 7 days for quiescence as described above.

Yet another procedure for inducing quiescence is to transfer cells grown in the cytokine mixture described above to a medium containing a cell cycle inhibitor such as TGF-β or Macrophage Inhibitor Protein-α (MIP-α). Entrance of the cell population into a quiescent state is monitored as described above.

Induction of a quiescent state is also performed by growing a population of expanded cells on a layer of Dexter culture adherent cells. Such growth condition cause the expanding cells to enter the $G_0$ of $G_1$ phase of the cell cycle. Cells are monitored at 1, 2, 5, and 7 days of quiescence and described above.

EXAMPLES

Example 1

Introduction of quiescent stem cells into a mammal is accomplished by injection into a vein of a mammal, e.g., a human, dog, or mouse. Injection volumes in mouse models were the same in each experiment and ranged from 0.5 to 1.0 ml. A portion of the injected stem cells populate the bone marrow, spleen, and thymus. The injected stem cells or transfected stem cells can be from the host mammal (autologous transplantation) or the cells can be from a different mammal of the same species (allogenic transplantation).

An exemplary procedure for assessing engraftment by the method of the invention was performed as follows. Following the injection of 40×10$^6$ male BALB/c mouse bone marrow stem cells for each of five days into female BALB/c host mice, the percent of male cells or male DNA in host tissue at various times post transplantation was determined by standard cytogenetic techniques (Stewart, F. M. et al. (1993) Blood 81:2566–2571). This procedure allowed identification of male cells as those cells lacking heterochromatic staining at the centromere (c-banding).

Alternatively, Southern analysis using a labelled (e.g., radiolabelled) Y chromosome-specific DNA probe was used to analyze the percent engraftment of male donor cells into female host bone marrow as defined above. A useful Y chromosome-specific probe is the pY2 cDNA probe (Lamar, E. E. and Palmer, E. (1984) Cell 37:171), or other mouse Y chromosome-specific DNA probe which hybridizes to repetitive sequences on the murine Y chromosome.

Southern analysis to detect the degree of engraftment of male cells into female bone marrow was performed using standard techniques (see, e.g., Sambrook, et al. (1989) Molecular Cloning: A Laboratory Manual. Cold Spring Harbor Laboratory Press). Typically, DNA extracts of murine tissue (such as bone marrow) were prepared by lysis in 0.15 mol/L NaCl, 0.02 mol/L Tris, 0.02 mol/L EDTA, 1% sodium dodecyl sulfate (SDS), followed by purification using organic extraction with proteinase K, pancreatic RNAse, and phenol-chloroform followed by precipitation in ethanol. DNA samples were analyzed for the presence of Y chromosome-specific sequences using the pY2 cDNA probe. These samples were digested with the restriction enzymes DraI and BamHI, and the digested fragments were separated by gel electrophoresis in 0.8% agarose. Equal amounts of digested DNA, as determined by 260/280 ratios, were loaded per gel and the comparability of loaded DNA was determined by reprobing membranes with a partial- or full-length cDNA for interleukin-3 (IL-3) or other marker cDNA. The DNA fragments were transferred from the gel onto Zetaprobe nylon membranes (BioRad, Richmond, Calif.) according to established Southern blotting techniques. The pY2 probe was labeled with $^{32}$P using a random primer labeling kit (Boehringer Mannheim, Mannheim, Germany); hybridization with Zetaprobe membranes was performed in 10% dextran sulfate, 1% SDS, 1× Denhardt's, 4× SSCP at 65° C. for 18 to 22 hours. Autoradiography was performed using Kodak XRP x-ray film with or without enhancing screens (Eastman Kodak, Rochester, N.Y.) at −70° C. for varying time intervals. The percentage of male DNA in female host tissue was calculated based on densitometry comparisons between post-transplant DNA samples and male murine DNA. Densitometry was performed on an LKB ultrascan XL enhanced laser densitometer (LKB Pharmacia, Uppsala, Sweden). Calculations of percent DNA were adjusted based on amounts of DNA loaded on each gel as estimated by densitometry of IL-3-probed Southern blots. The detection limit for male DNA in a mixture of male and female DNA was approximately 3% under these conditions.

Example 2

Administration of a cell cycle inducing agent adversely affects the capability of the harvested cells to engraft in a non-myeloablated host prior to approximately 6 weeks post-transplantation. Bone marrow harvested from BALB/c mice six days after the mice had received 150 mg/kg 5-fluorouracil by tail vein injection was markedly inferior to normal bone marrow for long term engraftment, e.g., greater than approximately 6 weeks post-transplantation.

In these studies, two tibia/two femur equivalents (or approximately 40×10$^6$ bone marrow cells) of male marrow where transplanted by tail vein injection on each of five consecutive days into non-myeloablated female hosts. Engraftment was assessed in DNA of host female splenic and thymic tissues by Southern analysis of pY2 hybridizing sequences at 1, 2, 3, 10, and 20 months following the last transplantation. For host mice receiving bone marrow from 5-FU-treated male mice, the mean bone marrow engraftment was 8% at 3 months after transplantation as compared to 38% for host mice receiving bone marrow from untreated male mice. This 5-FU treatment defect has also been observed at 3 months post-transplantation in host female splenic and thymic tissues.

The engraftment defect seen after 5-FU treatment is a transient functional defect. Bone marrow cells from 5-FU-treated male mice six days after treatment were found by hydroxyurea suicide analysis to be in active cell cycle. In contrast, bone marrow cells harvested from 5-FU-treated male mice 35 days after treatment or from untreated male mice were not in active cell cycle and exhibited long term engraftment capabilities superior to those of 5-FU-treated cells (see Table 1).

TABLE 1

| | % Engraftment | |
|---|---|---|
| | Bone marrow | Spleen |
| Control donor marrow | 38.1 | 33.1 |
| Day 6 post 5-FU | 18.1 | 16.5 |
| Day 35 post6 5-FU | 35.3 | 32.9 |

% Engraftment values were determined by densitometry of Southern blots (not corrected for loading on the gel) on 4 or 5 mice per group.

Example 3

This experiment demonstrates that cytokine incubation of murine bone marrow cells impairs the capacity to repopulate in non-myeloablated hosts. Incubation of murine or human hematopoietic cells with various cytokine combinations has been used to expand stem cell populations and induce stem cell replication resulting in enhanced gene-carrying retroviral integration. This study examined the effect of a 48 hour in vitro incubation in cell culture medium (DMEM-Low glucose, 15% fetal calf serum) with a cytokine combination of murine IL-3-CHO (50 U/ml), murine IL-6 (50 U/ml), murine IL-11 (50 ng/ml), and murine SCF (50 U/ml) on engraftment of a first group of male donor bone marrow cells into non-myeloablated female BALB/c host mice. A second group of donor cells was incubated with medium alone, and a third group of donor cells was not incubated (FIG. 2).

In each group three injections of 40×10$^6$ cells per injection were made over three days. Engraftment was evaluated by Southern analysis using a Y chromosome-specific probe (pY2). Mean engraftment of male donor bone marrow cells into female BALB/c host mice was determined (y axis). For Group 1 host mice, donor cells were incubated for 48 hours in culture medium plus IL-3, IL-6, IL-11, and SCF. Three injections each of 40×10$^6$ cells were given to host mice. For Group 2 host mice, donor cells were incubated for 48 hours in culture medium alone. Three injections each of 40×10$^6$ cells were given to host mice. For Group 3 host mice, three injections each of 0.5 ml PBS (phosphate buffered saline lacking cells) were given to host mice. Donor cells administered to Group 4 mice were not incubated prior to giving three injections each of 40×10$^6$ cells to host mice.

Figure 2:
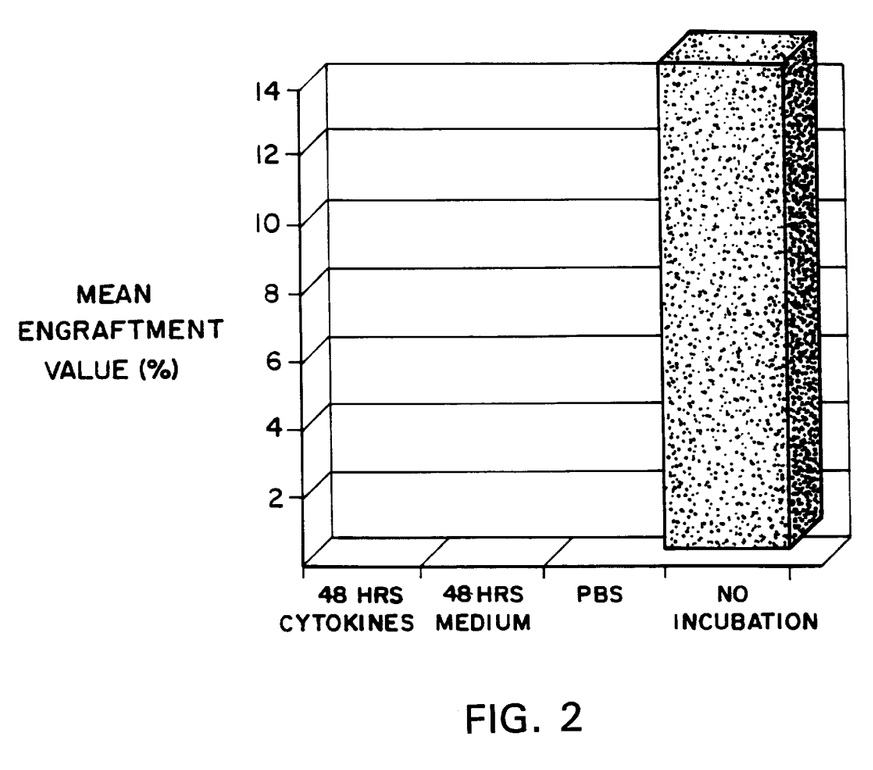
FIG. 2 is a bar graph showing the results of studies in which male BALB/c mouse bone marrow was incubated in culture media alone or in media plus cytokines.

Neither the cytokine-incubation group, nor the medium-only incubation group demonstrated evidence of male DNA sequence, indicating that no engraftment occurred (FIG. 2). The control group which received cells immediately after donor collection, showed a 16.6% engraftment level (range 11.6–24.8%, n=4) in host bone marrow. This result is consistent with the previous observation that pre-treatment with a cell cycle inducing agent, 5-FU, causes decreased engraftment, and indicates that exposure to cytokines and/or inducement of active cell cycling impairs engraftment and repopulating capacity of hematopoietic stem/progenitor cells in non-myeloablated hosts.

Figure 3A:
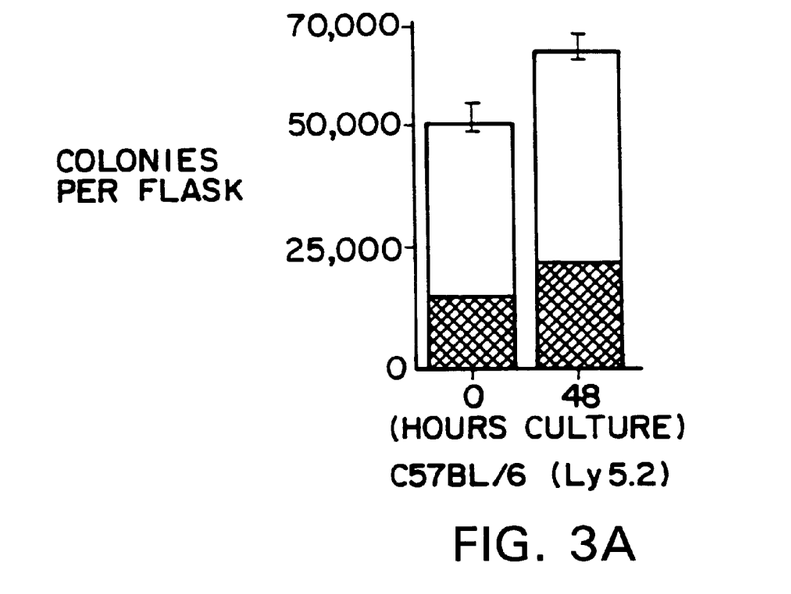
FIGS. 3A and 3B are bar graphs representing progenitor cell expansion of whole marrow in culture medium with the cytokines mSCF (mouse stem cell factor), IL-3, IL-6, and IL-11 for 48 hours for cell types Ly5.2 (3A) and Ly5.1 (3B), which cells differ in a single surface marker allowing engraftment of the different populations of cells to be monitored by anti-Ly5.2 antibody staining.
Figure 3B:
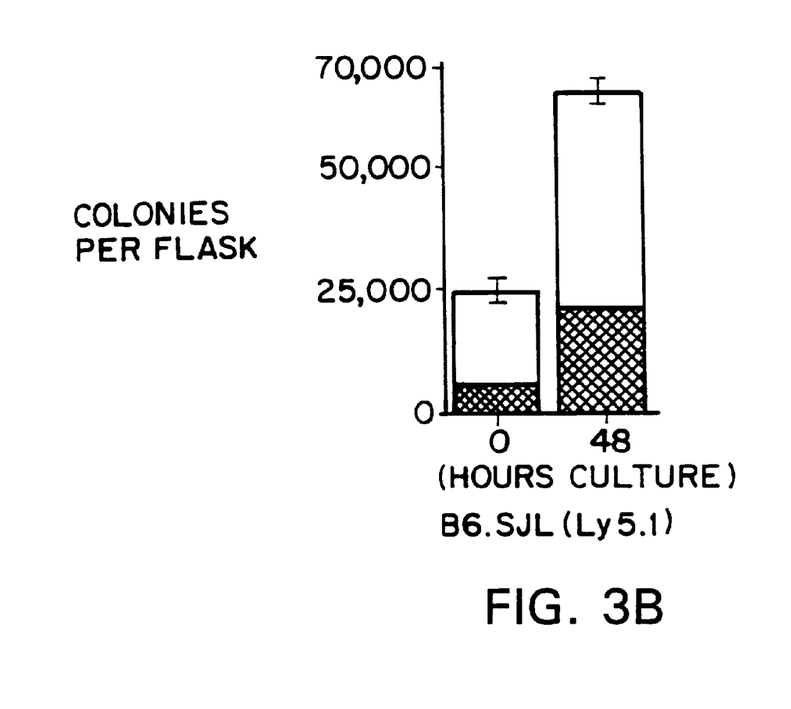

A similar cytokine-induced impairment of repopulating capacity was observed for cells from C57BL/6 (Ly5.2) mice and B6.SJL-Ly5a(Ly5.1) mice. FIGS. 3A and 3B show the progenitor cell content present in 10×10$^4$ noncultured (0 hours) cells, and that of culture flasks initiated with 10×10$^6$ cells after 48 hours of culture. CPP-CFC are represented by dark shaded bars (▨) at the bottom of the columns, and LPP-CFC are represented as lighter bars (□) at the top of the columns. Cultured marrow cells from C57BL/6 (Ly5.2) were expanded by 49% for HPP-CFC and 14% for LPP-CFC (FIG. 3A). Cells from B6.SJL-Ly5a (Ly5.1) were expanded by 206% for HPP-CFC and 166% for LPP-CFC (FIG. 3B). This expansion of noncultured progenitors by cytokine-treatment was significant for HPP-CFC and LPP-CFC in Ly5.1 marrow (P=0.01, Wilcoxon's rank sum test), and had a significance level of P=0.1 in Ly5.2 marrow.

Example 4

Cytokines are used for the in vitro expansion of hematopoietic progenitor/stem cells resulting in an increased percentage of stem cells in active cell cycling. An evaluation of the level of engraftment as a function of the cell cycle in which the population of donor cells reside was performed.

Figure 1A:
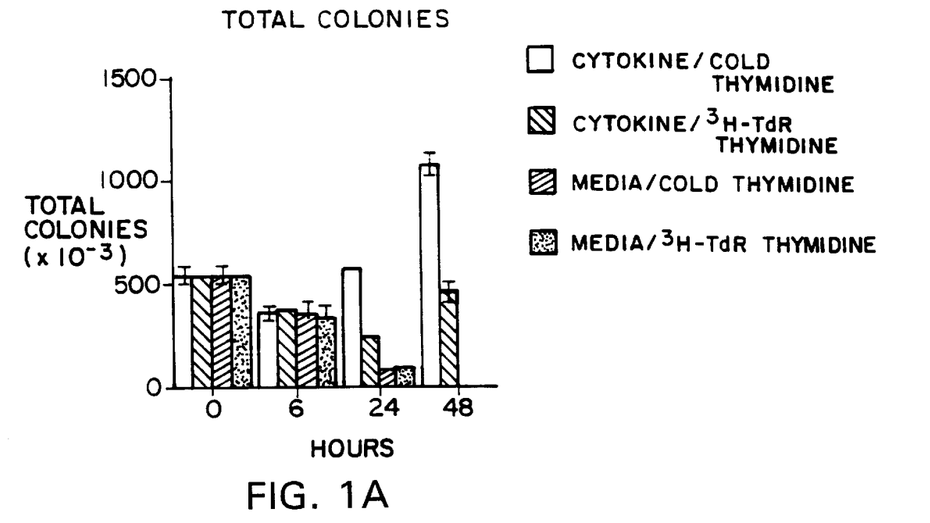
FIGS. 1A and 1B are graphs of the results of a study on the influence of preincubation of donor bone marrow cells in growth medium containing the cytokines IL-3, IL-6, IL-11, and SCF (stem cell factor).

Male BALB/c donor bone marrow cells were exposed in vitro to a combination of cytokines for enhancement of retroviral integration in vitro in primitive progenitor/stem cells. Male BALB/c mouse bone marrow was incubated in culture media alone or in media plus IL-3 (50 U/ml), IL-6 (50 U/ml), IL-11 (50 ng/ml), and steel factor (c-Kit ligand, 50 U/ml; Genetics Institute, Cambridge, MA) for 6, 24, or 48 hours (x axes of FIGS. 1A and 1B). High proliferative potential colony-forming cells (HPP-CFC) and total progenitors (>50 cell colonies) were determined per culture flask (y axes of FIGS. 1A and 1B). Cell cycle status was assessed by determining the percentage of cells traversing S phase (synthesizing DNA) by treating the cells in vitro with tritiated thymidine ($^3$HtdR) and determining the percentage of cells killed (FIGS. 1A and 1B).

Figure 1B:
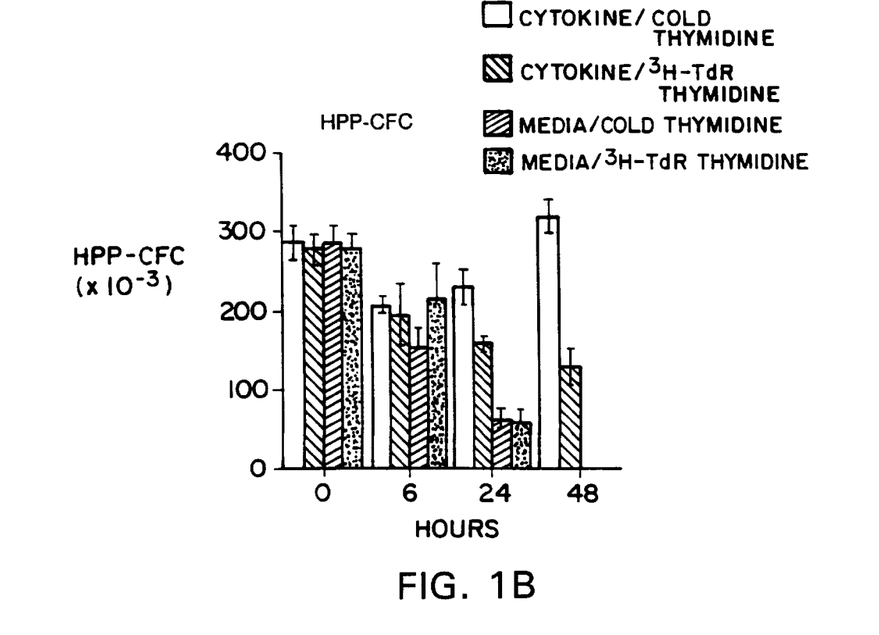

Donor cells were also evaluated for the effects of in vitro liquid culture on HPP-CFC (multi-factor responsive, FIG. 1A) and total progenitors (FIG. 1B). At initiation of the cultures, there was less than 3.5% killing in both the cytokine-exposed and media-only cell cultures indicating that the donor cells were in the quiescent ($G_1$ or $G_0$) phase (FIGS. 1A and 1B). There was a progressive increase in killing at 6, 24, and 48 hours (FIGS. 1A and 1B) in the cytokine-treated cell cultures. Donor bone marrow cells incubated in vitro with cytokines show a maintenance of multi-factor responsive HPP-CFC (111% of input, FIG. 1B) and an expansion of total progenitors (199% of input, FIG. 1A) with a concomitant progression from quiescence to active cell cycling. Initial $^3$HtdR killing was 3.5% and 1.0% of HPP-CFC (FIG. 1B) and total progenitor (FIG. 1A), respectively. After 48 hours the proportions of cells killed by exposure to $^3$HtdR were 60% (FIG. 1B) and 58% (FIG. 1A), respectively.

Figure 4A:
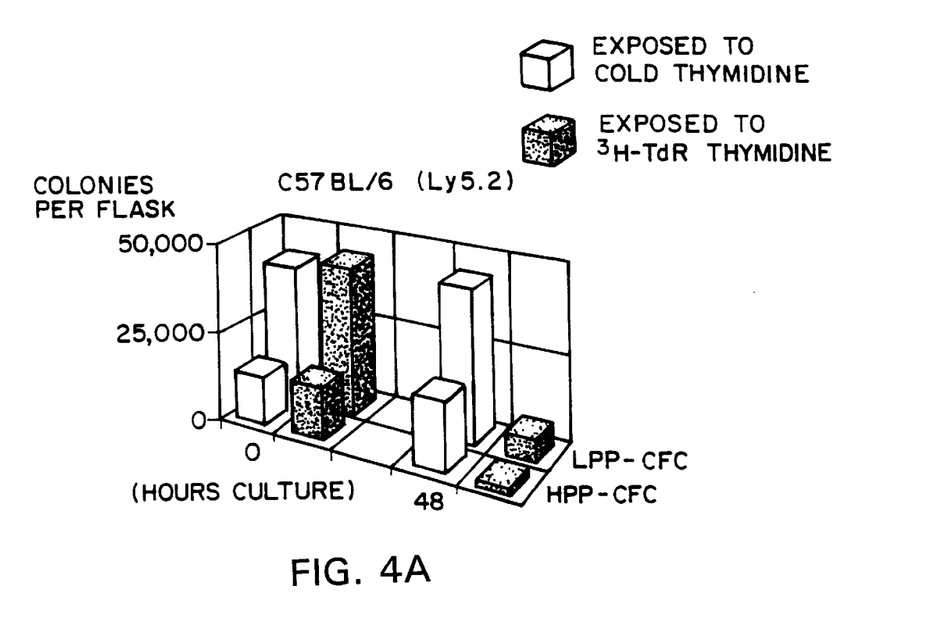
FIGS. 4A and 4B are three-dimensional bar graphs of a cell-cycle analysis, using a thymidine suicide assay, of noncultured cells (marrow) and cytokine-treated cells (progenitor cells) incubated for 48 hours in culture medium with the cytokines mSCF, IL-3, IL-6, and IL-11. The results for Ly5.2 cells are shown in FIG. 4A and the results for Ly5.1 cells are shown in FIG. 4B.
Figure 4B:
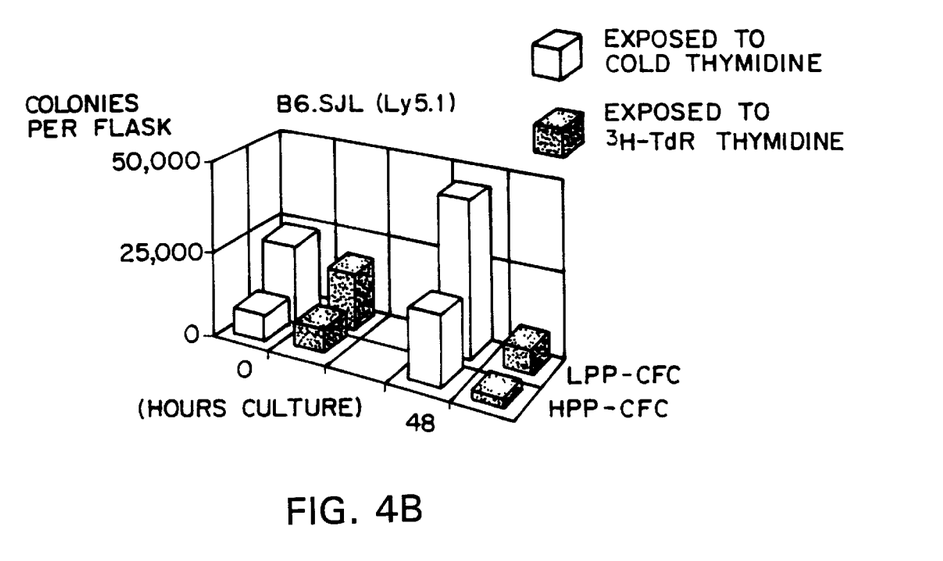

Cell-cycle analysis (thymidine suicide) of noncultured marrow and progenitor cells from C57BL/6 and B6.SJL/Ly5a mice, in which the cells were incubated for 48 hours in culture medium with the cytokines mSCF, IL-3, IL-6, and IL-11 is illustrated in FIGS. 4A and 4B. Bar graphs represent HPP-CFCs and LPP-CFCs present in $10 \times 10^4$ noncultured (0 hours) marrow cells and in $10 \times 10^4$ cultured marrow cells (48 hours) either short-term exposed (dark bars) or not exposed (light bars) to high activity tritiated thymidine ($^3$HTdR). HPP-CFC data are plotted in front, LPP-CFC data at the back.

The thymidine suicide assay of C57BL/6 (Ly5.2) progenitors showed no killing of LPP-CFCs and of HPP-CFCs at zero time, indicating that these progenitor cell populations were dormant (FIG. 4A). After 48 hours of culture with cytokines 86% of LPP-CFC and 95% of HPP-CFC were killed and thus progressing through S phase. The thymidine suicide assay of B6.SJL-Ly5a (Ly5.1) progenitors showed little kill of noncultured LPP-CFCs (32%) and HPP-CFCs (20%) (FIG. 4B). After 48 hours of culture with cytokines, 86% of LPP-CFC and 95% of HPP-CFC were killed and thus in cell-cycle progression. They had a mean of 0% in noncultured Ly5.2 (C57BL/6) marrow (FIG. 4A) and 20% in noncultured Ly5.1 (86-SJL-Ly5a) marrow (FIG. 4B). After culture with cytokines a mean of 95% and 98% of HPP-CFC were killed by exposure to high-activity tritiated thymidine in either strain, indicating that they had been induced to enter active phases of the cell cycle. That meant LPP-CFC killed was 0% in noncultured Ly5.2 marrow (FIG. 4A) and 32% in noncultured Ly5.1 marrow (FIG. 4B). Culture with cytokines induced killing at a mean of 86% of LPP-CFC in both strains. A standardized-normal test comparing the mean differences of noncultured and cultured progenitors was highly significant ($^P$<0.0001) in both strains.

Induction of stem cell expansion using steel factor alone at 50 ng/ml for 24–48 hours provides the same degree of cellular expansion as the combination of IL-3, IL-6, IL-11 and steel factor (data not shown).

Example 5

To determine the efficiency of engraftment of treated cells into a non-myeloablated host by scheduled administration over time, the following experiment was performed. Four groups of male mouse donor bone marrow cells were evaluated for engraftment into normal non-myeloablated BALB/c female mice. Staggered liquid marrow cultures were established and female BALB/c non-myeloablated hosts were transplanted with $40 \times 10^6$ noncultured male BALB/c bone marrow cells for three consecutive days (total of $120 \times 10^6$ cells) or the equivalent of $40 \times 10^6$ cultured cells exposed or not exposed to the cytokine regimen described above. At 35 days following the last transplantation, engraftment was evaluated by Southern blot analysis using the pY2 probe or by FISH analysis (Fluorescence In Situ Hybridization analysis, a standard technique well known to those of ordinary skill in the relevant arts). Non-cultured donor bone marrow cells showed a mean engraftment of approximately 15% while no engraftment was observed with cells cultured in media alone or media with cytokines (IL-3, IL-11, IL-6, and steel factor).

Example 6

Exposure of donor bone marrow cells to cytokines is useful to enhance retroviral integration for the formation of transfected cells. The efficiency of engraftment of transfected cells was examined to evaluate the usefulness of such cells in a gene therapy regimen.

Male BALB/c bone marrow cells were transfected with a retroviral vector carrying the MDR gene to produce transfected cells. The transfection protocol involved inducing the cells into cell cycle by cytokine exposure and provided over 90% MDR transfection into the primitive stem cells (HPP-CFC). The transfected cells were transplanted into female BALB/c mice on 5 consecutive days (one transplantation per day for a total of $45 \times 10^6$ cells transplanted over 5 days). Following the last transplantation, the mice were treated three times with Taxol (10 mg/kg IP) over 7 months to expand the MDR-carrying stem cells in vivo. At 14 months following transplantation, the recipient mice were sacrificed for analysis of engraftment and the presence of the MDR gene.

There was a 8.9% to 13.4% engraftment of male transfected cells into female hosts as determined by Southern analysis using the pY2 probe. However, there was only minimal expression in 3 of 4 transplanted animals of the MDR gene as determined by RT-PCR (reverse transcriptase-polymerase chain reaction). Thus, cycling murine stem cells successfully integrated the MDR gene following retroviral infection in vitro, but very few of the cells which engrafted were carrying the gene. This suggests that dormant Go cells without the retroviral gene construct were able to engraft, and that a critical feature of successful engraftment is the use of dormant cells. Effective gene transfer requires that the stem cells be returned to a quiescent state prior to transplantation.

Example 7

This example describes the ability to enhance engraftment by administering non-cycling cells. The competitive assay used cells from Ly5.2/Ly5.1 mice which allow engraftment to be monitored by immunoassay for the presence of cells having the Ly5.2 cell surface marker.

Bone marrow cells were cultured with cytokines for 48 hours to induce cellular expansion. Bone marrow cells were obtained by flushing tibias and femurs of 6- to 8-week-old Ly5.2 (C57BL/6) and Ly5.1 (B6.SJL-Ly5a) mice. Ten million bone marrow cells were cultured in nonadherent tissue culture dishes at a density of $10^6$ nucleated cells/ml in DMEM (low glucose), supplemented with 15% heat-inactivated fetal calf serum (FCS) with cytokines (recombinant mouse SCF (rmSCF) at 50 ng/ml, rmIL-3 at 60

U/ml, rmIL-6 at 50 U/ml, and recombinant human IL-11 (rhuIL-11) at 50 ng/ml) at 37° C. in a fully humidified atmosphere of 5% $CO_2$ in air. After 48 hours all cultured cells were procured by vigorous pipetting with ice-cold phosphate-buffered saline (PBS) and cell scraping (as determined by microscopy).

The cell cycle status was analyzed by comparing colony growth of marrow exposed to high activity tritiated thymidine ($^3$H-TdR) to colony growth of marrow that was not challenged with radioactivity. The percentage of HPP-CFCs and LPP-CFCs killed by exposure to $^3$H-TdR indicate the fraction of HPC that underwent active DNA synthesis in cell cycle progression. No cell cycle activity could be detected in noncultured Ly5.2 (C57BL/6) marrow. The amount of HPP-CFC and LPP-CFC killed in noncultured fresh marrow by thymidine suicide was a mean of 0% indicating that most HPC were in dormancy. After culture with cytokines a mean of 95% of HPP-CFCs and a mean of 86% of LPP-CFCs were killed by exposure to high-activity tritiated thymidine in these Ly5.2 mice (FIG. 4A). This indicates that most of the cytokine-treated cells had been induced to enter active phases of the cell cycle.

This change of HPC cycle status induced by culture of marrow cells with cytokines was also observed in marrow from Ly5.1 (B6.SJL-Ly5a) mice (FIG. 4B). In this strain 20% of HPP-CFCs and 32% of LPP-CFCs of noncultured marrow were killed by exposure to $^3$H-TdR. The amount of progenitor cells entering active phases of the cell cycle increased dramatically as shown by HPP-CFC fractions of 98% and LPP-CFC fractions of 86% killed by exposure to high activity tritiated thymidine in this strain. A standardized-normal test comparing the mean differences of noncultured and cultured progenitors was highly significant ($P<0.0001$) in both strains.

Expansion of HPC was determined by comparing the contents of HPP-CFCs and LPP-CFCs of both freshly obtained uncultured marrow and cytokine-treated cells in a soft-agar colony assay. Cultured cells were procured by vigorous pipetting with ice-cold PBS and cell scraping until virtually no residual cells remained in the culture flasks as determined by microscopy. Cultured marrow cells from Ly5.2 (C57BL/6) and Ly5.1 (B6.SJL) mice were expanded by 49% and 206% for HPP-CFC (dark bars, FIGS. 3A and 3B, respectively), and 14% and 166% for LPP-CFC (light bars, FIGS. 3A and 3B, respectively) in these murine strains. This expansion of cultured progenitors by cytokine-treatment was significant for HPP-CFC and LPP-CFC in Ly5.1 marrow ($P<0.01$. Wilcoxon's rank sum test). The significance level for Ly5.2 marrow was $P=0.1$.

A competitive Ly5.2/Ly5.1 transplantation assay was performed as follows. Recipient mice were exposed to 12.0 Gy (7.0 Gy and 5.0 Gy given 3 hours apart) in a gamma cell 40 cesium source and 1 hour later injected intravenously (IV) with (1) a mixture of 50% cytokine-cultured Ly5.1 cells (equivalent to $20\times10^6$ starting cells procured after 48 hours of incubation with cytokines) and 50% fresh noncultured Ly5.2 cells; (2) a mixture of 50% noncultured Ly5.1 cells (equivalent to $20\times10^6$ starting cells harvested after 48 hours of incubation with cytokines) and 50% cytokine-treated Ly5.2 cells; and (3) a mixture of 50% cytokine-cultured cells (equivalent to $20\times10^6$ starting cells harvested after 48 hours of incubation with cytokines) of both cell types. Volumes for injection ranged from 0.5 to 1.0 ml. The percentages of marrow cells bearing the Ly5.2 and Ly5.1 phenotypes were determined 12 and 22 weeks post-transplant by fluorescence-activated cell sorter (FACS) analysis. One million suspended cells were incubated for 10 minutes with mouse 1 gG (Sigma Chemicals, St. Louis, Mo., USA) for 30 minutes at 4° C. The Ly5-specific monoclonal antibodies for Ly5.2 (fluorescein isothiocyanate [FTTC]-conjugated monoclonal antibody 1042.1) and Ly5.1 (biotin-conjugated A201.7) (Jackson Immunolaboratories) were added for 30 minutes, and then washed twice. Cell-bound biotinylated monoclonal antibody A201.7 was detected with streptavidin-Red 670 (R&D, Minneapolis, Minn., USA), which was incubated for 30 minutes at 4° C. Cells were washed twice and subsequently analyzed with an FACS (FACS-STAR:Becton Dickinson Immunosystems, San Jose, Calif.).

Figure 5A:
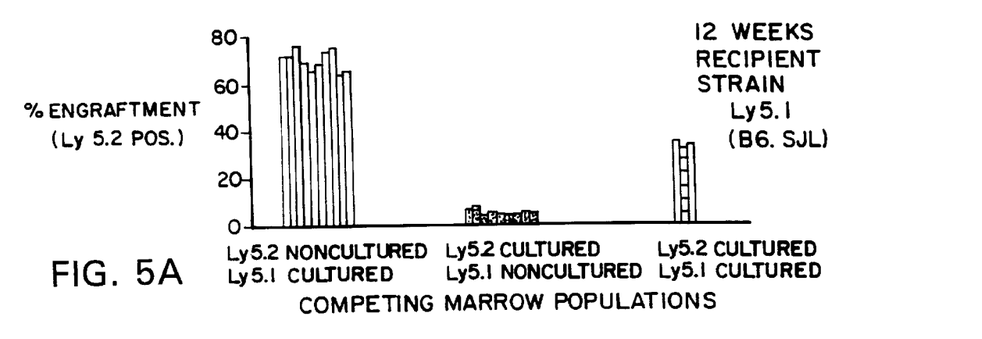
FIGS. 5A to 5C are graphs of bone marrow engraftment after competitive transplantation of noncultured cells with cytokine-treated cells. FACS (Fluorescent Activated Cell Sorting) analysis of donor-derived cells stained with monoclonal antibodies specific for Ly5.2 was performed at 12 weeks (5A and B) and 22 weeks (5C). The percent engraftment as a function of culturing or non-culturing is presented.
Figure 5B:
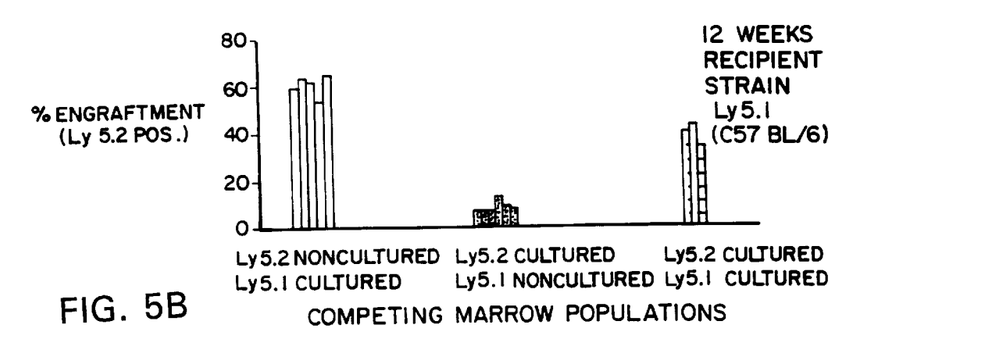
Figure 5C:
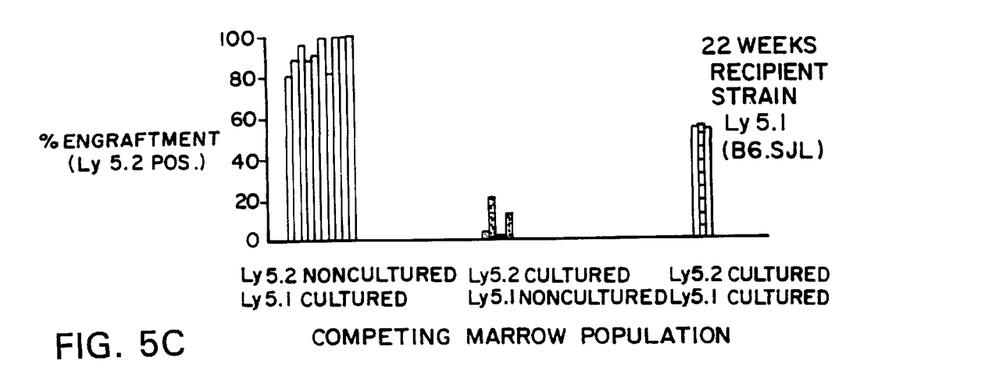

Bone marrow engraftment was assessed after competitive transplantation of noncultured with cultured marrow cells by FACS analysis for donor-derived cells stained with monoclonal antibodies specific for the two alleles of Ly-5 (FIGS. 5A to 5C). Columns represent the marrow fraction of individual mice positive for anti-Ly5.2 antibody staining. Analysis of anti-Ly5.1 antibody straining gave reciprocal results (data not shown). FIG. 5A represents analysis at 12 weeks post-transplantation in Ly5.1 (B6.SJL-Ly5a) recipients; noncultured Ly5.2 (C57BL/6) marrow competed with Ly5.1 marrow led to mean ($\pm$SE) engraftment levels of 70%$\pm$1% (n=10) for the Ly5.2 cells; cytokine-cultured Ly5.2 marrow cells competing with Ly5.1 cells led to 5%$\pm$1% (n=10) engraftment. Differences in engraftment between noncultured and cytokine-treated populations were significant ($P<0.01$, Wilcoxon's rank sum test). FIG. 5B represents analysis at 12 weeks post-transplantation in recipient mice of Ly5.2 background. Noncultured Ly5.2 cells competing with Ly5.1 cells led to 63%$\pm$5% (n=5) engraftment for the Ly5.2 cells; cultured Ly5.2 cells competing Ly5.1 cells contributed to 7%$\pm$2% (n=5) engraftment. Differences in engraftment were significant at a level of $P=0.1$. Analysis at 22 weeks post-transplantation in recipient mice of Ly5.1 background is shown in FIG. 5C. Noncultured Ly5.2 marrow cells contributed a mean of 93%$\pm$2% (n=10) to engraftment whereas cytokine-treated Ly5.2 cells gave a mean engraftment of 4%$\pm$2% (n=10) when compared with Ly5.1 marrow cells. Differences in engraftment between noncultured and cytokine-treated populations were significant at 22 weeks post-transplantation ($P<0.01$).

Example 8

A cytokine-induced engraftment defect was observed when cytokine treated and untreated cells from male and female mice were administered to a myeloablated host. Engraftment was assessed by monitoring the presence of male stem cells administered to a female myeloablated host using the Y chromosome as a marker.

Cells obtained from BALB/c mice were cultured as described above for the Ly5.2/Ly5.1 competitive assay. Female recipient mice were given 10.5 Gy irradiation in doses of 5.5 Gy and 5.0 Gy administered 3 hours apart and 1 hour later injected intravenously with either a mixture of 50% cytokine-cultured female (corresponding to the equivalent of $20\times10^4$ starting cells harvested after 48 hours of culture with cytokines) and 50% ($20\times10^4$) fresh noncultured female cells. Volumes for injection were the same in each experiment and ranged from 0.5 to 10 ml. The percentage of male marrow in host marrow cells was then determined 10 and 14 weeks post-transplantation using Southern blot analysis with the Y-chromosome-specific pY2 probe (Lamar, E. E. and Palmer, E., Cell 37:171, 1984) and performed as described (see Example 1).

Briefly, approximately 5 μg of genomic DNA per sample was digested with the restriction enzyme Dra-1 (Boehringer Mannheim, Indianapolis, Ind.) and separated by gel electrophoresis in 0.8% agarose (GIBCO-BRL). DNA fragments were transferred onto Zetaprobe nylon membranes (BioRad, Richmond, Calif.) by capillary transfer overnight in 0.4 N sodium hydroxide. The blots were probed for the presence of Y-specific sequences using pY2-cDNA. Autoradiography was performed on Kodak XRP films (Eastman Kodak, Rochester, N.Y.). The percentage of radioactivity of male and female DNA was quantified by exposing filters to photostimulatable phospor imaging plates (Molecular Dynamics, Sunnyvale, Calif.) and scanning the plates with a 400 Å PhosphorImager (Molecular Dynamics) (Johnston, R. F. et al., Electrophoresis 11:355, 1990) and quantitation was based on comparisons between post-transplant DNA samples and male murine DNA. Calculations of percent DNA were adjusted based on amounts of DNA loaded on each gel as determined by separate probing with a cDNA which hybridizes specifically to IL-3.

A competitive transplant assay was performed using the equivalent of $20 \times 10^6$ starting male or female cells obtained after a culture with the cytokines mSCF, IL-3, IL-6, and IL-11. Cells subjected to cytokine treatment for 48 hours were progressing through the cell cycle (see Example 4, supra). The cells were mixed and injected together with fresh, noncultured cells of the opposite gender into irradiated (10.5 Gy) recipient mice. Southern blot engraftment analysis using the Y-chromosome-specific pY2 cDNA probe showed compromised engraftment of cultured cytokine-exposed marrow cells competing with noncultured marrow cells in bone marrow, spleen, and thymus of lethally irradiated female hosts at 10 and 14 weeks post-transplantation. Noncultured male BALB/c marrow cells, competing with cytokine-cultured female BALB/c marrow, lead to mean engraftment ($\pm$SE) levels of 70%$\pm$2% (n=5) in female BALB/c recipient marrow at 10 weeks post-transplantation. Mean engraftment levels of cultured male marrow cells competing with noncultured female cells were 13%$\pm$9% (n=5) in the marrow of female recipients at 10 weeks. This difference in engraftment of noncultured and cytokine-treated populations is statistically significant at a level of P=0.5 (Wilcoxon's rank sum test). The engraftment defect was greater 14 weeks after transplantation. Fresh noncultured male BALB/c marrow cells competing with cytokine-treated female cells contributed to 95%$\pm$9% (n=10) marrow engraftment while cytokine-treated male cells competing with noncultured female cells gave a mean level of only 2%$\pm$1% (n=10). Differences in engraftment between non-cultured and cytokine-treated populations were highly significant (P<0.01). In these BALB/c transplants the engraftment defect was also apparent when spleen and thymus were analyzed, indicating that this is a general engraftment defect.

Studies using both engraftment models showed an increased engraftment defect at longer time intervals post-transplantation, suggesting that the most striking effect may be on long-term repopulating stem cells.

In the transplant models involving lethal whole-body irradiation, the possibility of a contribution from host marrow repopulation was excluded. Irradiated female mice were injected with male cells and repopulation was by male cells only. Similar controls werE performed and results obtained in the Ly5.2/Ly5.1 model.

Statistical analysis was performed using levels of significance of expansion of non-cultured progenitors by cytokine-treatment analyzed by Wilcoxon's rank sum test (Freund, J. E. and Walpole, R. E., Mathematical Statistics (ed. 3). Englewood Cliffs, N.Y., Prentice-Hall, 1980, p. 478). Mean differences of percentages of noncultured and cultured progenitors killed by in vitro $^3$HTdR exposure were compared by standardized-normal tests (Freund, J. E. and Walpole, R. E., Mathematical Statistics (ed. 3). Englewood Cliffs, N.Y., Prentice-Hall, 1980, p. 478). Differences in engraftment of noncultured and cytokine-treated populations were compared by Wilcoxon's rank sum test.

Example 9

Preparation of quiescent stem cells for transplantation can be accomplished by a number of different techniques. In a first method, noncycling stem cells are isolated from a mammal which has not been treated with a cell cycle inducing agent for a period of time sufficient to allow at least 50%, preferably at least 70%, most preferably at least 80% of the stem cells to return to the quiescent $G_1$ or $G_0$ phase of the cell cycle. Such quiescent bone marrow stem cells are used directly for transplantation into a non-myeloablated mammal.

Actively cycling stem cells can be isolated from a mammal treated with a cell cycling inducing agent or the harvested stem cells can be treated in vitro with a cell proliferation agent, e.g., a cytokine, to increase the number of stem cells or to enhance in vitro retroviral infection for use in ex vivo gene therapy. Subsequently, actively cycling stem cells are induced to become quiescent by removing nutrients from the culture medium, e.g., serum starvation, causing at least 50%, preferably at least 70%, more preferably at least 80% of the cells to enter the $G_0$ cell cycle phase. The quiescent stem cell population is then transplanted into a host mammal.

Example 10

The efficiency of engraftment in the first weeks post-transplantation was examined using the BALB/c mouse model described herein. Bone marrow from male BALB/c mice was incubated for 48 hours in the presence of IL-3, IL-6, IL-11, and Steel factor, as described above. These cells were mixed in approximately equal proportions with untreated female BALB/c mouse bone marrow. The mixture was administered to female BALB/c mice which had been lethally irradiated (1100 rads). As indicated herein, such conditions led to very low efficiency of engraftment of the male cytokine-treated cells when observed after 10 or more weeks post-transplantation. However, when engraftment was observed at one week post-transplantation, engraftment of the cytokine-treated cells was superior to untreated cells.

Treatment of the early repopulating stem cells with a cytokine results in cell expansion. Cytokine-treated stem cells engraft with high efficiency during the first approximately 6 weeks, and as early as one week, after engraftment. Thus, stimulating early repopulating stem cells to enter the cell cycle enhances their ability to engraft, making such cells useful for transplantation or ex vivo gene therapy requiring early (and short-term) engraftment of the cells, e.g., for gene therapy to treat transient conditions such as tumors.

Cytokine-treated stem cells exhibit very low long term engraftment. In the preceding examples, untreated cells were found in the engrafted population, while no detectable cytokine-treated cell progeny were observed at 22 weeks post-transplantation. Cells known to be quiescent were shown herein to engraft at a higher efficiency relative to cytokine-treated cells when long-term engraftment is monitored, where long term is a time greater than approximately 6 weeks post-transplantation.

A method of maximizing efficiency of short and long term engraftment is an embodiment of the present invention. Bone marrow replacement or the effects of gene therapy are rapidly achieved by maximizing short term engraftment. Maximizing long term engraftment is useful in patient treatment situations which require extended effects such as in long term gene therapy.

Short term engraftment is achieved in a host mammal by treating stem cells appropriate for engraftment with a cytokine or combination of cytokines to induce proliferation as described herein. If gene therapy is a desired treatment, the cells are transfected with an exogenous gene of interest while actively progressing through the cell cycle. While the cytokine-treated cells continue to progress through the cell cycle, a fraction of the cells are administered to a myeloablated or non-myeloablated host mammal. Cells treated in this manner engraft with high efficiency and remain in the bone marrow population during the approximately first 6 weeks post-transplantation.

According to the method of the invention, the remaining fraction of the cells are induced to become quiescent prior to transplantation. As described herein, cells which are not actively cycling engraft at a high efficiency at times greater than approximately 6 weeks post-transplantation.

As a result of such administration of cycling and non-cycling stem cells, both early and long term effects bone marrow transplantation or gene therapy are achieved, enhancing the ability to effectively treat the patient. Long term gene therapy is more suited for genetic defects or enzymatic deficiencies.

Alternatively, populations of stems cells enriched in short or long term repopulating stem cells may be obtained and these populations administered to the host mammal to maximize the efficiency of short or long term engraftment. Such a method would include first obtaining a population of pluripotent hematopoietic stem cells and inducing the population of cells to expand. The early repopulating stem cells are separated from the late repopulating stem cells by a stem cell sorting technique such as the technique described above under General Procedures. The population enriched with actively cell cycling early stem cells is introduced into the host mammal if short term engraftment is desired. The population enriched with late repopulating stem cells is induced to become quiescent prior to introduction into the host mammal if long term engraftment is desired.

The above method is used for ex vivo gene therapy by including the step of transfecting the expanded cells with exogenous DNA by retroviral integration, for example, prior to the stem cell separation step.

Use

Diseases that are treated by transplantation of bone marrow stem cells and for which treatment can be enhanced by the methods of the invention include, but are not limited to, diseases such as lymphoma, multiple myeloma, breast cancer, testicular cancer, leukemias, congenial hemolytic anemias (sickle cell anemia and thalassanemia) and some immunodeficiency diseases (e.g., acute leukemia, Hodgkin's and non-Hodgkin's lymphoma, and neuroblastoma).

Several human diseases can be treated by ex vivo gene therapy involving transplantation of transfected bone marrow stem cells, and such treatment can be enhanced by the methods of the invention. Correction of human inherited disorders in bone marrow stem cells in tissue culture has been shown for Gaucher disease in which the mutant glucocerebrosidase-encoding gene is replaced by the wild type gene. Dihydrofolate reductase deficiency in which a mutated form of the dihydrofolate reductase-encoding gene (DHFR) is replaced has been performed in mice (Watson, J. D. et al., Recombinant DNA, 2nd ed., pp. 571–576).

Ex vivo gene therapy in large animals such as humans presents several difficulties that can be alleviated by enhancement of stem cell engraftment following transplantation of quiescent cells. In one set of studies using macaque monkeys, bone marrow cells from the monkeys were infected with a vector carrying a human cDNA for adenosine deaminase. The donor monkeys received total body irradiation and then an infusion of infected cells. Only low levels of expression of human adenosine deaminase-encoding cDNA could be detected in these mammals. Similar results were obtained in experiments with bone marrow cells that carried the human β-globin gene (Watson, J. D. et al., Recombinant DNA, 2nd ed., pp. 571–576). Such reduced expression can be enhanced by the method of the invention in which quiescent transfected stem cells are transplanted into the non-myeloablated recipient mammal. Finally, transfer of a normal human adenosine deaminase gene (ADA) into a human patient for the treatment of severe combined immune deficiency caused by a mutation in ADA has been achieved with encouraging results using bone marrow-stem cell gene therapy in humans (Watson et al. (1992), supra, p. 578). However, the treatment required that the patients receive gene-corrected cells every 1 to 2 months for up to one year before showing signs of clinical improvement. The instant invention is useful in enhancing the engraftment at each treatment and thereby more quickly and assuredly improve the health of the patient.

What is claimed is:

1. A method of preparing a stem cell composition, said method comprising:
   a) providing a population of pluripotent hematopoietic stem cells;
   b) expanding said population of stem cells to yield a population of expanded stem cells; and
   c) inducing a majority of the cells in said population of expanded stem cells to become quiescent, and using said quiescent stem cells as the cell composition.

2. A method of preparing a stem cell composition, said method comprising:
   a) providing a population of pluripotent hematopoietic stem cells;
   b) expanding said population of stem cells to yield a population of expanded stem cells;
   c) transfecting said expanded stem cells with exogenous DNA to generate a population of transfected stem cells; and
   d) inducing a majority of the cells in said population of transfected stem cells to become quiescent, and using said quiescent transfected stem cells as the cell composition.

3. A method for preparing a stem cell composition, said method comprising:
   a) providing a population of pluripotent hematopoietic stem cells;
   b) expanding said population of stem cells to yield a population of expanded stem cells;
   c) transfecting said expanded stem cells with exogenous DNA to generate a population of transfected stem cells, said population comprising early repopulating stem cells and late repopulating stem cells;
   d) separating said early repopulating stem cells from said late repopulating stem cells; and
   e) inducing a majority of the cells in said population of transfected late repopulating stem cells to become quiescent, and using said quiescent transfected late repopulating stem cells as the cell composition.

4. The method of claim 1 further comprising a step of transplanting said stem cell composition into the host mammal in a series of administrations, wherein
   i) a first portion of said stem cell composition is administered to the host at a first point in time; and
   ii) thereafter, additional portions of said stem cell composition are administered in at least five and not greater than fifteen additional adminstrations, each spaced from the other by at least 12 hours.

5. A method of preparing a stem cell composition comprising first and second dosage units to provide short term and long term engraftment of said stem cells, said method comprising:
   a) providing a population of pluripotent hematopoietic stem cells;
   b) expanding said population of stem cells to yield a population of expanded stem cells;

c) dividing said population of expanded stem cells into a first fraction and a second fraction, and using said first fraction as the first dosage unit of the stem cell composition; and d) inducing a majority of the cells in said second fraction to become quiescent stem cells, and using said quiescent stem cells as the second dosage unit of the stem cell composition.

6. A method of preparing a stem cell composition comprising first and second dosage units, said method comprising:

a) providing a population of pluripotent hematopoietic stem cells;

b) expanding said population of stem cells to yield a population of expanded stem cells;

c) transfecting said expanded stem cells with exogenous DNA to generate a population of transfected stem cells;

d) dividing said population of transfected stem cells into a first fraction and a second fraction, and using said first fraction as the first dosage unit of the stem cell composition; and e) inducing a majority of the cells in said second fraction to become quiescent transfected stem cells, and using said second fraction as the second dosage unit of the cell composition.

7. The method of claim 1, wherein the host mammal is a non-myeloablated mammal.

8. The method of claim 1, wherein the host mammal is a myeloablated mammal.

9. The method of claim 1, wherein said stem cells are selected from the group consisting of allogenic bone marrow cells, autologous bone marrow cells, peripheral-blood cells, peripheral-blood stem cells, and cord blood stem cells.

10. The method of claim 1, wherein said stem cells are expanded by contacting said cells with a cytokine under conditions for cell proliferation.

11. The method of claim 10, wherein said cytokine is selected from the group consisting of Steel factor, IL-3, IL-11, and IL-6, or any combination thereof.

12. The method of claim 10, wherein said cytokine is Steel factor.

13. A stem cell composition comprising a population of pluripotent hematopoietic stem cells, wherein said population is first induced to expand, and is thereafter treated to induce a majority of the cells in said population to become quiescent.

14. A stem cell composition comprising a population of pluripotent hematopoietic stem cells transfected with exogenous DNA, wherein said population is first induced to expand, and is thereafter treated to induce a majority of the cells in said population to become quiescent.

15. A stem cell composition of claim 14, wherein said stem cells consist essentially of late repopulating pluripotent hematopoietic stem cells.

16. A stem cell composition comprising two dosage units, wherein said first dosage unit consists essentially of a population of expanded stem cells, and said second dosage unit consists essentially of the stem cell composition of claim 13.

17. The composition of claim 13, wherein said stem cells are selected from the group consisting of allogenic bone marrow cells, autologous bone marrow cells, peripheral-blood cells, peripheral-blood stem cells, and cord blood stem cells.

18. The composition of claim 13, wherein said stem cells are expanded by contacting said cells with a cytokine under conditions for cell proliferation.

19. The composition of claim 18, wherein said cytokine is selected from the group consisting of Steel factor, IL-3, IL-11, and IL-6, or any combination thereof.

20. The composition of claim 18, wherein said cytokine is Steel factor.

* * * * *